Figure 1:
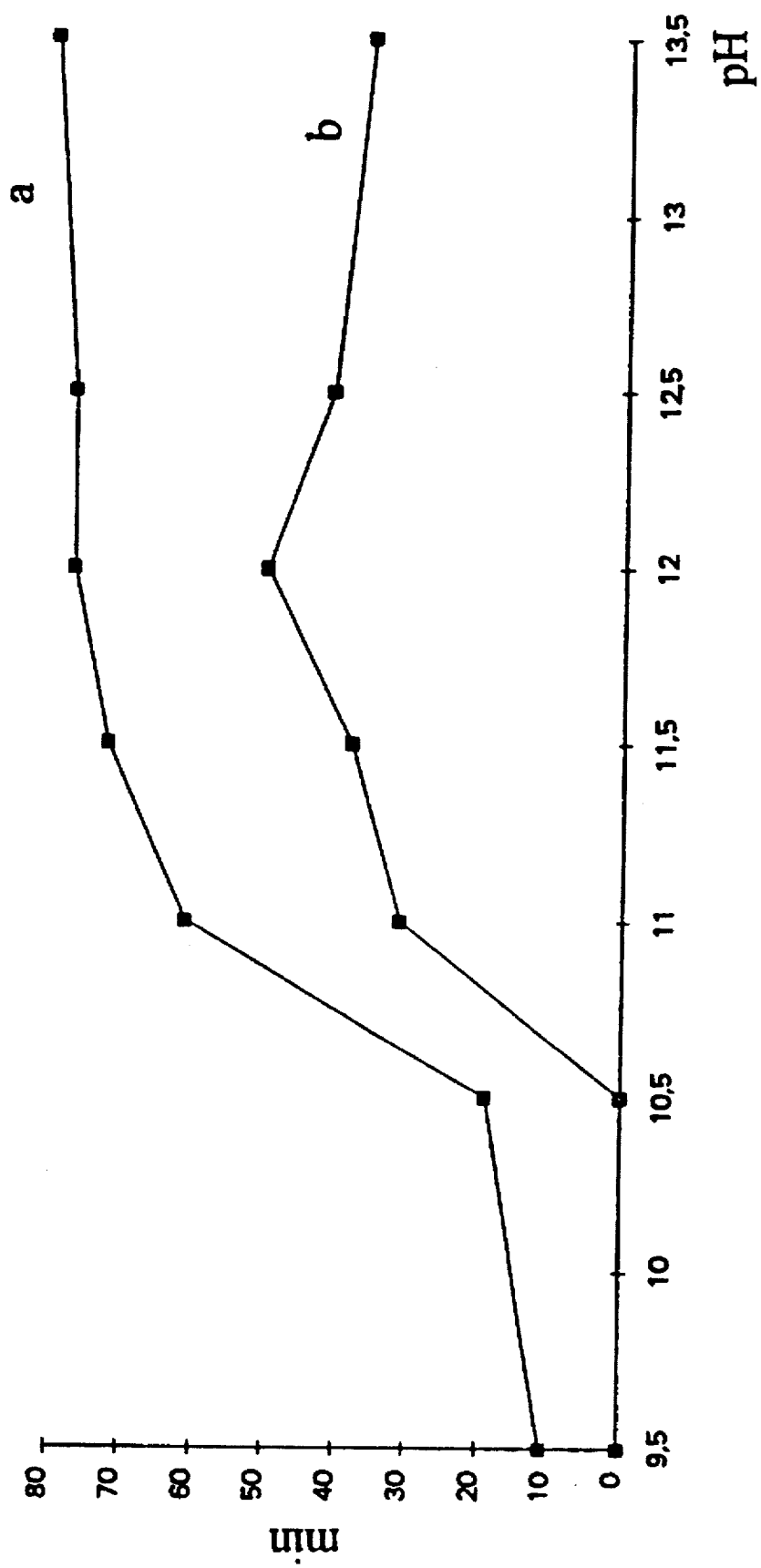

United States Patent [19]
Kalt et al.

[11] Patent Number: 5,628,941
[45] Date of Patent: May 13, 1997

[54] PROCESS FOR THE PRODUCTION OF CELLULOSE MOULDED BODIES

[75] Inventors: Wolfram Kalt, Lenzing; Heinrich Firgo, Vöcklabruck; Johann Männer, Weyregg; Eduard Mülleder, Linz; Bruno Mangeng, Linz; Arnold Nigsch, Vöcklabruck; Franz Schwenninger, Lenzing; Christoph Schrempf, Bad Schallerbach, all of Austria

[73] Assignee: Lenzing Aktiengesellschaft, Austria

[21] Appl. No.: 454,320

[22] PCT Filed: Feb. 1, 1995

[86] PCT No.: PCT/AT95/00021

§ 371 Date: Jun. 5, 1995

§ 102(e) Date: Jun. 5, 1995

[87] PCT Pub. No.: WO95/23827

PCT Pub. Date: Sep. 8, 1995

[30] Foreign Application Priority Data

Mar. 1, 1994 [AT] Austria ................. 430/94

[51] Int. Cl.⁶ .......... C07C 291/00; D01F 2/24; D01F 13/02
[52] U.S. Cl. .......... 264/38; 264/187; 564/297; 564/298
[58] Field of Search ........... 264/38, 187; 564/297, 564/298

[56] References Cited

U.S. PATENT DOCUMENTS 4,324,593  4/1982  Varga ...................... 106/203

FOREIGN PATENT DOCUMENTS

| 399519 | 5/1995 | Austria. |
|---|---|---|
| 47929 | 3/1982 | European Pat. Off. . |
| 356419 | 2/1990 | European Pat. Off. . |
| 427701 | 5/1991 | European Pat. Off. . |
| 553070 | 7/1993 | European Pat. Off. . |
| 2000082 | 7/1971 | Germany. |
| 218104 | 1/1985 | Germany. |
| 229708 | 11/1985 | Germany. |
| 254199 | 2/1988 | Germany. |
| WO93/11287 | 6/1993 | WIPO. |

OTHER PUBLICATIONS

English language absract of AT 399,519 (published May 26, 1995).

English language absract of DD 218,104 (published Jan. 30, 1985).

English language abstract of DD 254,199 (published Feb. 17, 1988).

English language abstract of DE 2,000,082 (published Jul. 15, 1971).

English language abstract of EP 47,929 (published Mar. 24, 1982).

English language abstract of EP 427,701 (published May 15, 1991).

English language abstract of EP 356,419 (published Feb. 28, 1990).

English language abstract of EP 553,070 (published Jul. 28, 1993).

*Primary Examiner*—Leo B. Tentoni
*Attorney, Agent, or Firm*—Brumbaugh, Graves, Donohue & Raymond

[57] ABSTRACT

The invention is concerned with a process for the production of cellulose moulded bodies. In this process, cellulose is first dissolved in an aqueous solution of a tertiary amine-oxide, in particular N-methylmorpholine-N-oxide (NMMO), to produce a mouldable cellulose solution. Second, the cellulose solution is molded and conducted into an aqueous precipitation bath, wherein the cellulose is precipitated, which produces a moulded body and a spent precipitation bath. Next, the spent precipitation bath is regenerated. This regenerated aqueous amine-oxide solution is re-used to dissolve cellulose, thereby repeating the process. In the above process, the repeated aqueous amine-oxide solution has a pH within certain defined limits.

23 Claims, 2 Drawing Sheets

PROCESS FOR THE PRODUCTION OF CELLULOSE MOULDED BODIES

BACKGROUND OF THE INVENTION

The present invention is concerned with a process for the production of cellulose moulded bodies, and a regenerated, aqueous solution of an amine-oxide used for the production of a mouldable cellulose solution.

For some decades there has been searched for processes for the production of cellulose moulded bodies able to substitute the viscose process, today widely employed. As an alternative which is interesting among other reasons for its reduced environmental impact, a method has been found for dissolving cellulose without derivatisation in an organic solvent and extruding from this solution moulded bodies, e.g. fibres and films. Fibres thus extruded have received by BISFA (The International Bureau for the Standardization of man made fibers) the generic name Lyocell. By an organic solvent, BISFA understands a mixture of an organic chemical and water.

It has been shown that as an organic solvent, a mixture of a tertiary amine-oxide and water is particularly useful for the production of cellulose moulded bodies. As amine-oxide, basically N-methylmorpholine-N-oxide (NMMO) is used. Other amine-oxides are described e.g. in EP-A - 0 553 070. A method for the production of mouldable cellulose solutions is known e.g. from EP-A-0 365 419.

The cellulose is precipitated from the cellulose solution in an aqueous precipitation bath. During this process, amine-oxide builds up in the precipitation bath. To render the method economical, it is of decisive importance to recover and reuse nearly all of the amine-oxide. Thus the amine-oxide process presents the following 3 main steps:

(A) dissolving cellulose in an aqueous solution of a tertiary amine-oxide, in particular N-methylmorpholine-N-oxide (NMMO), to produce a mouldable cellulose solution, (B) moulding the cellulose solution and conducting the moulded cellulose solution into an aqueous precipitation bath, wherein the cellulose is precipitated, thus being obtained a moulded body and a spent precipitation bath, (C) regenerating, i.e. purifying and concentrating the spent precipitation bath, thus being obtained a regenerated aqueous amine-oxide solution which is used again in step (A) for dissolving cellulose.

The term "regenerating" is to be understood as any means capable of processing the precipitation bath so that an aqueous amine-oxide solution is produced, which can be used again in step (A). Such means include purification, treatment with ion exchangers, concentration, etc.

In the precipitation bath, not only amine-oxide but also degradation products of the cellulose and the amine-oxide build up. These may be heavily coloured, thus impairing the quality of the produced moulded bodies if they are not removed from the precipitation bath. Additionally, also metal traces may build up in the precipitation bath, leading to a reduced process safety.

In order to remove these degradation products, some proposals are known from the literature:

DD-A 254 199 describes a process for the purification of aqueous solutions of NMMO, according to which the solution passes through anion exchangers, wherein in a first step the anion exchanger contains an exchange resin of a styrene-divinylbenzene copolymerisate carrying tertiary amine groups of the -CH$_2$N(CH$_3$)$_2$ type and in a second step quaternary ammonium groups of the -CH$_2$N(CH$_3$)$_3$OH type as functional groups. It is described that the NMMO solution to be purified is dark at the beginning of the purification, brown to yellow after the first step and bright yellow to transparent after the second step.

A disadvantage of this process consists in that the solutions thus treated exhibit a high pH value, which subsequently requires a more complex purification. Additionally, in this already known process alkali and earth alkali cations, as well as partially basic degradation products (morpholine, N-methylmorpholine and other compounds) are not removed from the solution. The metal ions and alkali and earth alkali metal ions respectively lead to undesired precipitations and incrustations, unwanted non-dissolved substances in the solution, and a reduced process safety. Although it is possible to remove these substances by adding a precipitation agent with subsequent filtration or other separating means, these operations however introduce additional chemicals or require additional technical processing.

EP-A - 0 427 701 describes a process for the purification of aqueous amine-oxide solutions, according to which the purification is carried out in a one-step process with an anion exchanger which as functional groups exclusively carries quarternary tetraalkyl ammonium groups of the formulas -CH$_2$N$^+$(CH$_3$)X$^-$ or -CH$_2$N$^+$(CH$_3$)$_2$(CH$_2$OH)X$^-$, X$^-$ representing the anion of an inorganic or organic acid, whereafter the anion exchanger is regenerated with an aqueous acidic solution. The anion X$^-$ preferably stems from a volatile acid, in particular carbonic acid, formic acid or acetic acid. These acids are also proposed for the regeneration of the anion exchanger.

In the International Patent Application WO93/11287 it is proposed to carry out the regeneration of the anion exchanger with an aqueous solution of a strong inorganic acid and subsequently with aqueous sodium hydroxide. It is further proposed to conduct the solution before or preferably after passing the anion exchanger through a cation exchanger. It is described that when employing a strong basic anion exchanger, the colouring of the exchanger resin produced by conducting the solution to be purified is so heavy that a mere regeneration with aqueous sodium hydroxide does not suffice to discolour the resin again. Therefore to maintain the capacity of the resin, it must be treated additionally with a strong inorganic acid.

The procedure described in WO93/11287 involves increased use of chemicals and obliges to use strong irritant substances, e.g. hydrochloric acid. Additionally it can be deduced from Example 5 of WO93/11287 that even when employing this process, the discolouring capacity of the anion exchanger after 10 operation cycles is reduced to nearly half of the original value.

A disadvantage of the amine-oxide process in contrast to the viscose process is the low thermal stability of the amine-oxides and in particular of the cellulose solution. This means that at the elevated process temperatures (approximately 110°–120° C.) there may be triggered off uncontrolled, highly exothermic decomposition processes in the cellulose solutions, which processes due to the development of gases may lead to heavy deflagrations or explosions and subsequently even to fires.

There is very little evidence found in the literature about the thermally unstable nature of the cellulose solution. The first clear reference to this phenomenon was made in 1986 by Buijtenhuijs et al. Especially in the presence of metal ions, the decomposition reactions in the spinning material may run away. On account of the metal construction of the plant components however, metal ions in the solution can never be excluded.

This runaway reaction cannot be prevented even by the addition of the stabiliser gallic acid propyl ester (GPE)

widely used today (Buijtenhuijs et al., 1986). On the contrary, as studies have shown, GPE and also other aromatic hydroxy compounds having good complexing properties increase still further the thermal instability of the NMMO-cellulose solution in the presence of metals; this means that GPE (co)triggers the dangerous running away or the explosions. This is described in the Austrian Patent Application A 1857/93, published on Oct. 15th, 1994.

From U.S. Pat. No. 4,324,593, a process for the production of a mouldable solution containing cellulose dissolved in a solvent is known. The solvent contains a tertiary amine-oxide and a compound which increases the dissolution rate of the cellulose. As such compounds, particularly primary, secondary, tertiary amines, aqueous ammonium and alkali hydroxides are cited, tertiary amines being preferred. The authors of the patent suppose that the accelerating effect of these compounds is due primarily to the fact that they increase the pH of the solution. Evidence for the validity of this supposition however is not provided, and neither it is indicated which pH the solution should have. Only in Claim 27 of U.S. Pat. No. 4,324,593, a general reference is made to the fact that the accelerating compound should have a pH of more than 7, and in the Examples XIV and XV the pH of a mixture consisting of solid tertiary amine-oxide, cellulose and water with sodium hydroxide and aqueous ammonium respectively is adjusted to pH of 14 and 12.3 respectively.

In U.S. Pat. No. 4,324,593 it is proposed to add the accelerating compound to the solvent in such an amount that it represents up to 20% of the mass of the finished solution, suggesting that in each individual case the amount should depend on the amine-oxide used.

In order to prevent degradation of NMMO and cellulose, it is known from DD-A-0 218 104 to add to the amine-oxide one or more basic substances in amounts of from 0.1 and 10 mole %, based on the cellulose solution. As basic substances, alkali hydroxides, e.g. NaOH, basically reacting salts, e.g. $Na_2CO_3$, as well as organic nitrogen bases are recommended.

SUMMARY OF THE INVENTION

It is an object of the present invention to develop the amine-oxide process in such a way that it is possible in a simple manner both to increase the thermal stability of the cellulose solution and to keep the degradation of cellulose as low as possible. Particularly it is an object of the present invention to remove the degradation products and impurities cited above which build up in the precipitation bath from the process.

The process according to the invention for the production of cellulose moulded bodies presents the following steps:
(A) dissolving cellulose in an aqueous solution of a tertiary amine-oxide, in particular N-methylmorpholine-N-oxide (NMMO), to produce a mouldable cellulose solution,
(B) moulding the cellulose solution and conducting the moulded cellulose solution into an aqueous precipitation bath, wherein the cellulose is precipitated, thus being obtained a moulded body and a spent precipitation bath,
(C) regenerating the spent precipitation bath, thus being obtained a regenerated aqueous amine-oxide solution which is used again in step (A) for dissolving cellulose, and is characterized in that in step (A) a regenerated, aqueous amine-oxide solution is used which has a pH value in a range whose upper and lower limits are defined, depending on the concentration of tertiary amine-oxide, by the equation $$pH = -0.0015 \times A^2 + 0.2816$$

A being the concentration of tertiary amine-oxide in the aqueous solution, expressed in % by weight of the aqueous solution, and fulfilling the condition $$40\% \leq A \leq 86\%,$$

preferably $$70\% \leq A \leq 80\%,$$

and f having a value of 1.00 for the upper limit and a value of −1.80, preferably −1.00, for the lower limit.

BRIEF DESCRIPTION OF THE PREFERRED EMBODIMENTS

The invention is based on the finding that the stability of the cellulose solution depends to a large extent on the pH the regenerated, aqueous amine-oxide solution used to prepare the suspension has. According to the present Patent Application, it is considered that a cellulose solution is the more stable the higher its thermal stability determined by means of DSC (Differential Scanning Calorimetry) is and the lower the simultaneous degradation of cellulose is, which is evidenced by a high polymerisation degree of the cellulose and a high viscosity of the cellulose solution.

According to the invention it has been shown that the thermal stability of cellulose solutions rises sharply when an aqueous amine-oxide solution having a pH of 10.5 or more is used to prepare them. The thermodynamically most stable cellulose solutions are those which are prepared from an aqueous amine-oxide solution having a pH in the range of from 11.5 to 12.5, the maximum thermal stability being obtained at a pH of 12.0.

Furthermore the invention is based on the finding that starting at a pH of at least 10.5, the polymerisation degree of the cellulose decreases significantly less, i.e., that significantly less cellulose is decomposed. The maximum of this positive effect lies also in a pH range of from 11.5 to 12.5. This means that the highest thermal stability of the cellulose solution and the highest stability of the cellulose against degradation are to be found in the same pH range and thus coincide. Also the viscosity measurements carried out on cellulose solutions show that there is least cellulose decomposed when the employed amine-oxide solution has a pH of at least 10.5. Below 10.5, the viscosity decreases sharply.

Therefore the process according to the invention is preferably carried out in a way that the regenerated, aqueous amine-oxide solution employed in step (A) exhibits a pH value in the range of from 10.5 to 13.5, more preferred in a range of from 11.5 to 13.5, and most preferred in a range of from 13.5 to 12.5.

The pH value of the regenerated, aqueous amine-oxide solution may be adjusted in a simple way by contacting the spent precipitation bath with an alkaline anion exchanger and optionally afterwards with an acidic cation exchanger.

Furthermore it has proved advantageous to adjust the pH value of the regenerated aqueous amine-oxide solution by contacting the spent precipitation bath with an adsorbing resin modified with alkaline groups, afterwards with an alkaline anion exchanger and at least partially with an acidic cation exchanger.

The entire precipitation bath or only a partial stream thereof may be contacted with the modified adsorbing resin and the ion exchangers, depending on the extent of the discolouration, the content of cations and anions and the desired final pH of the regenerated solution.

It has been shown that by using adsorbing resins and ion exchangers, not only the pH value of the NMMO solution may be adjusted in a simple way, but also the degradation products causing discolouration which have built up in the precipitation bath may be removed in a particularly effective way. Additionally the embodiment including the adsorbing resin ensures the possibility to regenerate the subsequent anion exchanger substantially without additional chemicals, e.g strong irritant acids. The adsorbing resin used according to the invention differs from the weak basic anion exchanger employed in the first step of DD-A 254 199 in that it is not a weak basic anion exchanger in the strict sense, but a resin destined not for the exchange but for the adsorption of substances. For this reason, an adsorbing resin also exhibits a special macroporous pore structure. Additionally the resin is modified to a lesser extent with weak basic groups than it is common in an anion exchanger.

It has been shown that the use of an adsorbing resin modified in this way for regenerating the precipitation bath does not only provide a more efficient removal of discoloured substances from the solution, but that also the regenerability of the resin is markedly better than that of the anion exchangers described in the literature.

Furthermore it has been shown that the use of an adsorbing resin prevents irreversible discolourations of the anion exchanger subsequently provided and therefore no significant capacity loss in the anion exchanger exceeding the specifications of the manufacturer occurs. This allows a sufficient regeneration of the anion exchanger with aqueous alkali hydroxide, e.g. with aqueous sodium hydroxide. Thus the additional use of strong acids may be avoided. Therefore another preferred embodiment of the process according to the invention uses an anion exchanger exclusively regenerated with aqueous alkali hydroxide and/or volatile organic acids.

By providing the cation exchanger subsequently to the anion exchanger, it is possible to compensate in a simple way and without additional chemical or mechanical means the hydroxide surplus resulting from the contact with the anion exchanger which significantly raises the pH value. Additionally cations are removed efficiently from the solution.

Advantageously the adsorbing resin modified with basic groups exhibits tertiary amino groups as functional groups. Tertiary amino groups such as groups of the $-CH_2N(R)_2$ type, R being alkyl, hydroxyalkyl etc., are known as weak alkaline groups with ion exchanging effect and enhance the discolouring effect in combination with the adsorbent effect of the adsorbing resin.

Additionally the anion exchanger advantageously exhibits quaternary ammonium groups as functional groups. These groups, e.g. of the $-CH_2N^+(CH_3)_3$ or $-CH_2N^+[(CH_3)_2(CH_2OH)]$ type, are known as strong basic functional groups with ion exchanging effect and fulfil the objective of removing undesired anions from the solution in the process according to the invention in an especially efficient way.

The cation exchanger advantageously exhibits sulfonic acid groups as functional groups. Sulfonic acid groups are known in cation exchangers.

Furthermore the stability of the cellulose solution can be additionally improved by introducing before, during or after regeneration of the precipitation bath, additionally to the alkaline substance, a substance having an antioxidative effect, that is to say an antioxidant.

The term "antioxidant" is to be understood to include all substances and mixtures of substances which counteract the oxidative and radical degradation of cellulose. Naturally, this term also includes scavengers and reducing agents. These substances include e.g. polyphenols, polyvalent oxycarbonic acids, trioxybenzenes etc. known from DE-A - 2 000 082. Preferred antioxidants are tannins and those substances cited in EP-B - 0 047 929, i.e., glyceraldehyde and/or one or more organic compounds having at least four carbon atoms and at least two conjugated double bonds and at least two hydroxyl and/or amino groups having at least one hydrogen atom. Pyrocatechol, pyrogallol, gallic acid and the methyl, ethyl, propyl and isopropyl esters of gallic acid are especially preferred. Hydroquinone, anthraquinone and structurally analogous compounds as well as their derivatives may be used as antioxidants.

The invention is also concerned with a regenerated aqueous solution of a tertiary amine-oxide, particularly NMMO, for the production of a mouldable cellulose solution having a pH value in a range whose upper and whose lower limits, depending on the concentration of tertiary amine-oxide, are defined by the equation $$pH=-0.0015 \times A^2 + 0.2816 \times A + f,$$

A being the concentration of tertiary amine-oxide in the aqueous solution, expressed in % by weight of the aqueous solution, and fulfilling the condition $$40\% \leq A \leq 86\%,$$

preferably $$70\% \leq A \leq 80\%,$$

and f having a value of 1.00 for the upper limit and a value of −1.80, preferably −1.00, for the lower limit.

The amine-oxide solution regenerated according to the invention preferably has a pH in the range of from 10.5 to 13.5, more preferred in a range of from 11.5 to 13.5, and particularly preferred in a range of from 11.5 to 12.5.

The invention will be explained in more detail by the following Examples. As the cellulose solutions, in each case kneaded spinning materials were used which were produced using NMMO solutions having pH values in a range of from 9.5 to 13.5. All percentages are % by weight.

The measurements of the pH values were carried out in each case using a pH electrode in the form of a single-stick measuring chain (Metrohm 6.0210.100) at 50° C., with an adjustment time of 90 seconds.

(1) Preparation of the kneaded spinning materials

The kneaded spinning materials were prepared according to the following general procedure:

Into a 250 ml beaker, gallic acid propyl ester and hydroxylamine were introduced as stabilisers in amounts corresponding to 0.03% and 0.05% respectively of the cellulose employed. Afterwards 221 g of an aqueous 72.46% NMMO solution having a pH in the range of from 9.5 to 13.5 (the pH was adjusted with NaOH and/or $H_2SO_4$) were added, stirred for 5 minutes at room temperature, and then the obtained solution was put into a laboratory kneader.

The beaker was dried with 25.5 g fibrous, air-dried (approximately 94%) cellulose, and then also the cellulose was put into the kneader.

The mixture was suspended for 15 minutes at room temperature and 250 mbar and afterwards heated (thermostat regulation: 130° C.). At approximately 90° C., the first drop of water distilled off, indicating the beginning of the dissolution. After 5 minutes, the vacuum was increased in time intervals of 25 mbar each up to 50 mb. The end of the dissolution process was reached approximately after 1 hour.

According to this general procedure, 7 kneaded spinning materials were prepared from 7 aqueous NMMO solutions. The NMMO solutions presented the following pH values: 9.5, 10.5, 11.0, 11.5 12.0, 12.5 and 13.5.

(2) Thermal stability of the spinning materials

The thermal stability of the spinning materials was determined both for spinning materials freshly produced and for spinning materials which had been heated before to 110° C. for 20 hours.

The tests on thermal stability were carried out according to Buijtenhuijs et al. (The Degradation and Stabilisation of Cellulose Dissolved in N-Methylmorpholine-N-Oxide (NMMO), in "Das Papier", 40th year, volume 12, pages 615–619, 1986) by means of the DSC (differential scanning calorimetry) technology (equipment: Mettler Druck DSC Thermosystem 4000), employing the process described in Austrian Patent Application A1857/93.

Configuration of the pressure-DSC:

For control and evaluation: TA-processor TC11;

Evaluation software: TA72AT.2; measurement: pressure DDK measuring cell DSC27HP; installed printer: Epson FX 850.

Test conditions:

The spinning material to be tested (5.8 mg±0.3 mg) is weighed in a cooled solid state into a perforated aluminium cup (open system) and subsequently intimately contacted with a homogeneous mixture of 9 parts by weight of $Fe_2O_3$ (manufacturer: Aldrich, type No. 3924) and 1 part by weight of metallic copper (manufacturer: Merck, type No. 2715), in a ratio of 2:1 (2 parts of spinning material:1 part of mixture).

To carry out the DSC-measurement, the measuring chamber was pressurized to 20 bar nitrogen after introducing the aluminium cup into it. Then heating was carried out at a rate of 10° C./min up to a temperature of 112° C. (starting at 40° C.). Afterwards the specimen was kept for a period 120 minutes maximum at 112° C., and during this time the DSC curve was recorded. Both parts of the process, heating to 112° C. and keeping at this temperature, were stored in the processor of the DSC equipment and interrelated by the latter always under the same conditions.

As initiation point in the DSC curve, the value which gives the first rising into the exotherm range was defined. As "onset" the time was defined at which the straight line resulting from the extrapolation of the base line before occurring of the effect cuts the tangent to the curve caused by the effect.

The following Table 1 relates the pH value of the NMMO solution used to prepare the kneaded spinning material to the respective initiation point (IP, in minutes) and onset-point (OP, in minutes), IP (th.) and OP (th.) referring to values of spinning materials which had been subjected to the thermal treatment mentioned above before the test was performed.

TABLE 1

| pH Value | IP | OP | IP (th.) | OP (th.) |
|---|---|---|---|---|
| 9.5 | 7 | 11 | 0 | 0 |
| 10.5 | 16 | 19 | 0 | 0 |
| 11.0 | 41 | 61 | 20 | 31 |
| 11.5 | 56 | 72 | 29 | 38 |
| 12.0 | 57 | 77 | 38 | 50 |

TABLE 1-continued

| pH Value | IP | OP | IP (th.) | OP (th.) |
|---|---|---|---|---|
| 12.5 | 60 | 77 | 30 | 41 |
| 13.5 | 60 | 80 | 26 | 36 |

FIG. 1 gives a graphic illustration of the correlation found, the pH value of the employed NMMO solution being plotted as the abscissa and the onset-point (in minutes) being plotted as the ordinate. The curve "a" shows the DSC-behaviour of spinning materials which have not been subjected to a thermal pretreatment, and the curve "b" shows the DSC-behaviour of thermally pretreated spinning materials.

From the results given in Table 1 and FIG. 1 respectively it can be seen that starting at a pH value of 10.5 of the NMMO solution used, the thermal stability of the obtained spinning material rises sharply and that at a pH of 11.5, particularly in the case of thermally pretreated spinning materials, the stability rises again. The maximum stability can be observed at a pH of about 12.0.

(3) Polymerisation degree (DP) of the cellulose

The following Table 2 relates the polymerisation degree of the dissolved cellulose before and after a thermal treatment of the kneaded spinning material (20 hours at 110° C.) to the pH value of the NMMO solution used to prepare the kneaded spinning material.

TABLE 2

| pH Value | DP | DP (th.) |
|---|---|---|
| 9.5 | 580 | 450 |
| 10.5 | 590 | 450 |
| 11.0 | 600 | 480 |
| 11.5 | 590 | 520 |
| 12.0 | 600 | 540 |
| 12.5 | 600 | 500 |
| 13.5 | 590 | 490 |

Figure 2:
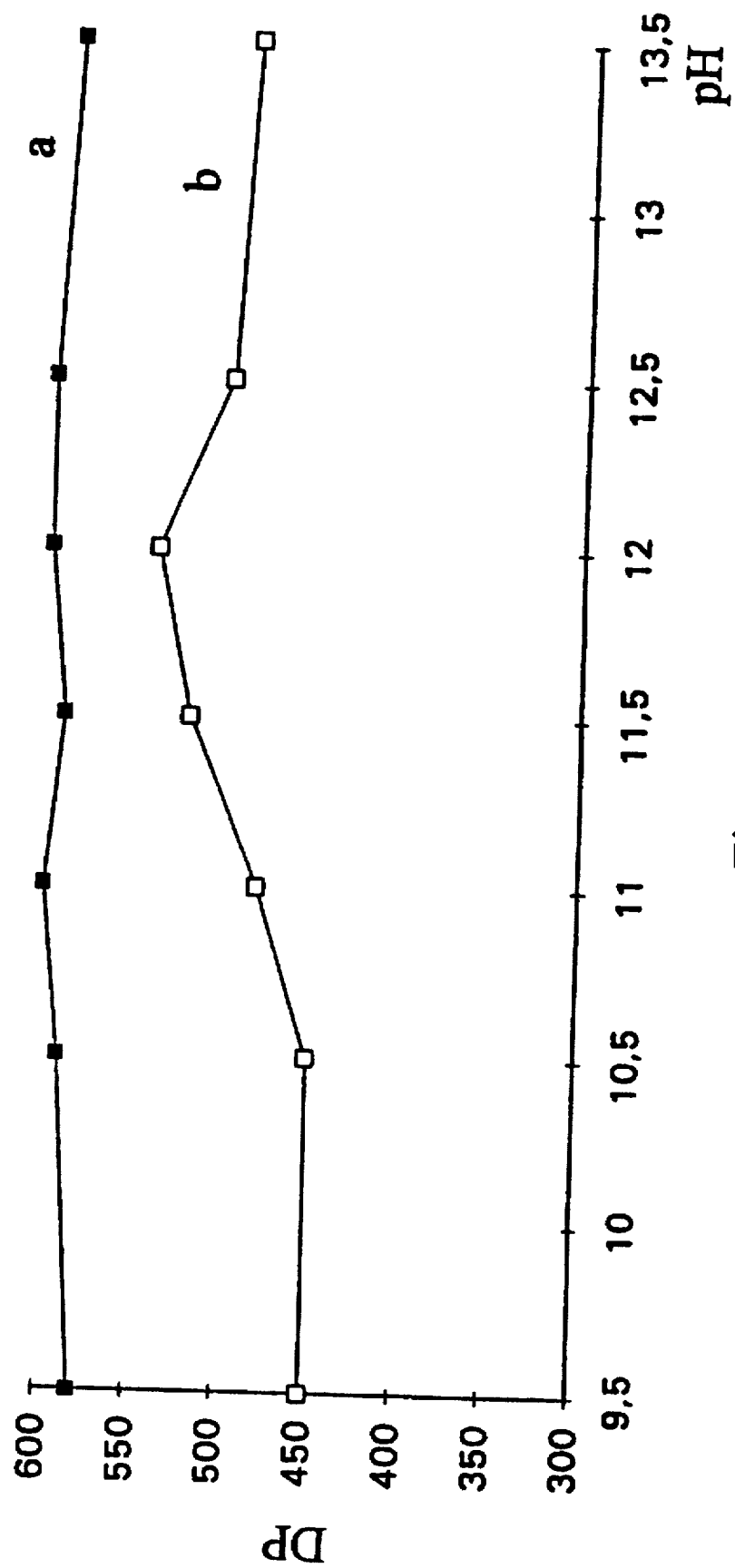

The results given in Table 2 are shown graphically in FIG. 2, the curve "a" showing the DP of the cellulose in the freshly produced spinning materials and the curve "b" showing the DP of the cellulose in spinning materials subjected to thermal treatment. From curve "a" it can be seen that the polymerisation degree of the cellulose in fresh spinning material practically does not depend on the pH value of the used NMMO. However, after having been thermally treated (curve "b") it can be seen that the polymerisation degree decreases at a lower rate when the pH of the spent NMMO solution lies in a range of from 10.5 to 13.5, the least decrease being observed again at a pH of 12.0.

(4) Use of an adsorbing resin and of ion exchangers for the adjustment of the pH value and for purification An aqueous liquid containing NMMO, consisting of a spent precipitation bath and other process liquids of the NMMO process and containing approximately 15% of NMMO first was passed through an adsorbing resin of the XUS 40285.00 (DOWEX) type modified with tertiary amine groups as functional groups. This adsorbing resin was regenerated in cycles with diluted aqueous alkali hydroxide and washed neutral with water.

Then the liquid passed through the adsorbing resin was passed through an anion exchanger of the LEWATIT MP 500 type (BAYER). This anion exchanger contains quaternary ammonium groups as functional groups. The anion exchanger was regenerated with diluted aqueous sodium hydroxide and washed neutral with water. It was shown that even after several cycles no capacity loss exceeding the specifications of the manufacturer occurred at the anion exchanger.

Subsequently a part of the solution was passed through a cation exchanger of the LEWATIT SM type (BAYER) containing sulfonic acid groups as functional groups. After this treatment, this part was combined with the rest of the solution which had not been passed through the cation exchanger. After concentration to an NMMO content of 72%, the regenerated NMMO solution exhibited a pH of about 12.0. In this NMMO solution, there substantially was no evidence of unwanted substances, or the substances were present in amounts which have no negative effects.

We claim:

1. A process for preparing cellulose molded bodies comprising the steps of:

(a) dissolving cellulose in an aqueous solution of a tertiary amine-oxide to produce a moldable cellulose solution, (b) molding said cellulose solution, (c) conducting said molded cellulose solution into an aqueous precipitation bath, thereby precipitating a cellulose molded body and producing a contaminated precipitation bath, (d) purifying said contaminated precipitation bath, thereby producing a regenerated aqueous amine-oxide solution, wherein the regenerated aqueous amine-oxide solution has a pH value in a range defined by the equation:

$$pH = -0.0015 \times A^2 + 0.2816 \times A + f$$

wherein

A = the concentration of tertiary aqueous amine-oxide in said aqueous solution, $40\% \leq A \leq 86\%$, f = 1.00 for an upper limit of the pH range
   f = −1.80 for a lower limit of the pH range, and (e) re-using said regenerated aqueous amine-oxide solution as the aqueous solution of a tertiary amine-oxide in step (a).

2. A process for preparing cellulose molded bodies comprising the steps of:

(a) dissolving cellulose in an aqueous solution of a tertiary amine-oxide to produce a moldable cellulose solution, (b) molding said cellulose solution, (c) conducting said molded cellulose solution into an aqueous precipitation bath, thereby precipitating a cellulose molded body and producing a contaminated precipitation bath, (d) purifying said contaminated precipitation bath, thereby producing a regenerated aqueous amine-oxide solution, wherein the regenerated aqueous amine-oxide solution has a pH value in a range defined by the equation:

$$pH = -0.0015 \times A^2 + 0.2816 \times A + f$$

wherein

A = the concentration of tertiary aqueous amine-oxide in said aqueous solution, $40\% \leq A \leq 86\%$, f = 1.00 for an upper limit of the pH range f = −1.00 for a lower limit of the pH range.

3. A process according to claim 1 or claim 2, wherein $70\% \leq A \leq 80\%$.

4. A process for preparing cellulose molded bodies comprising the steps of:

(a) dissolving cellulose in an aqueous solution of a tertiary amine-oxide to produce a moldable cellulose solution, (b) molding said cellulose solution, (c) conducting said molded cellulose solution into an aqueous precipitation bath, thereby precipitating a cellulose molded body and producing a contaminated precipitation bath, (d) purifying said contaminated precipitation bath, thereby producing a regenerated aqueous amine-oxide solution, wherein the regenerated aqueous amine-oxide solution has a pH from 10.5 to 13.5, and (e) re-using said regenerated aqueous amine-oxide solution as the aqueous solution of a tertiary amine-oxide in step (a).

5. A process according to claim 1, wherein said regenerated aqueous amine-oxide solution has a pH of from 11.5 to 13.5.

6. A process according to claim 1, wherein said regenerated aqueous amine-oxide solution has a pH of from 11.5 to 12.5.

7. A process according to claim 1, wherein the pH of said regenerated aqueous amine-oxide solution is adjusted by introducing a substance into the precipitation bath before regenerating said spent precipitation bath, which substance influences the pH.

8. A process according to claim 1, wherein the pH of said regenerated aqueous amine-oxide solution is adjusted by introducing a substance into the precipitation bath while regenerating the precipitation bath, which substance influences the pH.

9. A process according to claim 1, wherein the pH of said aqueous solution of a tertiary amine-oxide is adjusted by introducing a substance into the aqueous solution of a tertiary amine-oxide after regenerating said spent precipitation bath, which substance influences the pH.

10. A process according to claim 1, wherein the pH of said regenerated aqueous amine-oxide solution is adjusted by contacting said contaminated precipitation bath with an alkaline anion exchanger which introduces an alkaline substance into the precipitation bath.

11. A process according to claim 10, wherein after contacting said contaminated precipitation bath with an alkaline anion exchanger, said contaminated precipitation bath is contacted with an acidic cation exchanger.

12. A process according to claim 1, wherein the pH of said regenerated aqueous amine-oxide solution is adjusted by (a) contacting the contaminated precipitation bath with an adsorbing resin modified with alkaline groups, (b) contacting the contaminated precipitation bath with an alkaline anion exchanger, thereby introducing an alkaline substance into the precipitation bath, and (c) contacting at least a portion of the contaminated precipitation bath with an acidic cation exchanger.

13. A process according to claim 12, wherein an anion exchanger is used which is regenerated using a regenerator selected from the group consisting of alkali hydroxide, volatile organic acids and combinations thereof.

14. A process according to claim 10, wherein a substance having an antioxidative effect is introduced into the contaminated precipitation bath before regenerating said precipitation bath.

15. A process according to claim 10, wherein a substance having an antioxidative effect is introduced into the precipitation bath while regenerating the precipitation bath.

16. A process according to claim 10, wherein a substance having an antioxidative effect is introduced into the aqueous solution of a tertiary amine-oxide after regenerating said precipitation bath.

17. A regenerated solution of tertiary amine-oxide produced by the process of:
  (a) providing a contaminated precipitation bath comprising an aqueous solution of a tertiary amine-oxide, and
  (b) purifying said contaminated precipitation bath, thereby producing the regenerated aqueous amine-oxide solution, wherein the regenerated aqueous amine-oxide solution has a pH value in a range defined by the equation:

$$pH=-0.0015 \times A^2 + 0.2816 \times A + f$$

wherein
  A=the concentration of tertiary aqueous amine-oxide in said solution, $$40\% \leq A \leq 86\%,$$

f=1.00 for an upper limit of the pH limit
  f=−1.80 for a lower limit of the pH limit.

18. A regenerated solution of tertiary amine-oxide produced by the process of:
  (a) providing a contaminated precipitation bath comprising an aqueous solution of a tertiary amine-oxide, and
  (b) purifying said contaminated precipitation bath, thereby producing the regenerated aqueous amine-oxide solution, wherein the regenerated aqueous amine-oxide solution has a pH value in a range defined by the equation:

$$pH=-0.0015 \times A^2 + 0.2816 \times A + f$$

wherein
  A=the concentration of tertiary aqueous amine-oxide in said solution, $$40\% \leq A \leq 86\%,$$

f=1.00 for an upper limit of the pH limit
  f=−1.00 for a lower limit of the pH limit.

19. A regenerated solution according to claim 17 or claim 18, wherein $70\% \leq A \leq 80\%$.

20. A regenerated solution according to claim 17, wherein the regenerated aqueous amine-oxide solution has a pH of from 10.5 to 13.5.

21. A regenerated solution according to claim 17, wherein the regenerated aqueous amine-oxide solution has a pH of from 11.5 to 13.5.

22. A regenerated solution according to claim 17, wherein the regenerated aqueous amine-oxide solution has a pH of from 11.5 to 12.5.

23. A regenerated solution according to claim 17, wherein the solution comprises a substance having an antioxidative effect.

* * * * *

UNITED STATES PATENT AND TRADEMARK OFFICE
CERTIFICATE OF CORRECTION

PATENT NO. : 5,628,941
DATED : May 13, 1997
INVENTOR(S) : Kalt, et al.

It is certified that error appears in the above-indentified patent and that said Letters Patent is hereby corrected as shown below:

Column 1, line 28, "A-O 365,419" should read --A-O 356 419--;

Column 4, line 1, that portion of the equation reading "0.2816" should read --0.2816 x A + f,--;

Column 4, line 55, "13.5" should read --11.5--.

Signed and Sealed this

Seventh Day of October, 1997

Attest:

BRUCE LEHMAN

Attesting Officer

Commissioner of Patents and Trademarks